(12) United States Patent
Sklar et al.

(10) Patent No.: US 7,109,041 B1
(45) Date of Patent: *Sep. 19, 2006

(54) DISPLAY OF RECEPTORS AND ANALYSIS OF BINDING INTERACTIONS AND DRUG LIBRARIES

(75) Inventors: Larry Sklar, Albuquerque, NM (US); Eric Prossnitz, Albuquerque, NM (US); Vilven Janeen, Albuquerque, NM (US); Donna Neldon, Los Lunas, NM (US)

(73) Assignee: Science & Technology Corporation @University of New Mexico, Albuquerque, NM (US)

( * ) Notice: Subject to any disclaimer, the term of this patent is extended or adjusted under 35 U.S.C. 154(b) by 605 days.

This patent is subject to a terminal disclaimer.

(21) Appl. No.: 10/101,870

(22) Filed: Mar. 21, 2002

Related U.S. Application Data

(62) Division of application No. 09/370,358, filed on Aug. 9, 1999, now Pat. No. 7,018,846.

(60) Provisional application No. 60/096,010, filed on Aug. 10, 1998.

(51) Int. Cl.
- *G01N 33/566* (2006.01)
- *C07K 1/00* (2006.01)
- *C12P 21/02* (2006.01)
- *C12N 1/20* (2006.01)
- *C07H 21/04* (2006.01)

(52) U.S. Cl. .................... 436/501; 435/7.21; 435/69.5; 435/252.3; 536/24.2; 536/23.5; 530/402

(58) Field of Classification Search ............ 435/6, 435/7.1, 7.2, 7.21, 69.5, 252.3, 320.1; 436/501; 530/350, 388.22, 402; 514/2; 536/23.5, 536/24.2
See application file for complete search history.

(56) References Cited

U.S. PATENT DOCUMENTS

| | | | |
|---|---|---|---|
| 4,275,149 A | | 6/1981 | Litman et al. |
| 4,665,020 A | | 5/1987 | Saunders |
| 5,405,784 A | | 4/1995 | Van Hoegaerden |
| 5,583,010 A | * | 12/1996 | Baumbach et al. ........ 435/69.1 |
| 5,601,992 A | | 2/1997 | Lerner et al. |
| 5,639,603 A | * | 6/1997 | Dower et al. .................. 435/6 |
| 5,698,685 A | | 12/1997 | Summerton et al. |
| 5,747,349 A | | 5/1998 | van den Engh et al. |

OTHER PUBLICATIONS

Fulton, RJ et al., Clinical Chemistry 43(9)1749-1756, 1997.*
Sarvazyan-NA et al., Biochemistry 41(12858-12867)2002.*
Eppler, MC et al., J. Biol. Chem. 267:22(15603-15612)92.*
Wang, Ning and Donald E. Ingber, "Probing Transmembrane Mechanical Coupling and Cytomechanics Using Magnetic Twisting Cytometry," Biochem. Cell Bio. vol. 73, pp. 327-335.
Sklar, Larry A., et al., "Regulation of Ligand-Receptor Dynamics by Guanine Nucleotides", Journal of Biological Chemistry, vol. 262, No. 1, pp. 135-139, Jan. 5, 1987.
Sklar, Larry A. et al., "Non-cellular Display for Real Time Flow Cytometric Analysis of Seven Transmembrane Receptors" *Biotechniques* May 2000;28(5):976-80, 982-5.

* cited by examiner

*Primary Examiner*—Elizabeth Kemmerer
*Assistant Examiner*—Michael Brannock
(74) *Attorney, Agent, or Firm*—Henry D. Coleman; R. Neil Sudol; William J. Sapone

(57) ABSTRACT

A display and method of preparing 7-transmembrane and other receptors for real-time kinetic analysis of binding interactions. The invention includes display on beads and in micelles for multi-well and flow cytometric analysis. The invention is useful for ligand discovery and drug action discovery, and G-protein response in particular.

8 Claims, 9 Drawing Sheets

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: synthetic peptide containing N-terminus
      modification
<221> NAME/KEY: MOD_RES
<222> LOCATION: (1)..(1)
<223> OTHER INFORMATION: modification by t-butoxycarbonyl (t-boc)

<400> SEQUENCE: 1

Phe Leu Phe Leu Phe
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide containing modification on
      N-terminus
<221> NAME/KEY: MOD_RES
<222> LOCATION: (1)..(1)
<223> OTHER INFORMATION: FORMYLATION

<400> SEQUENCE: 2

Met Leu Phe Phe Gly Gly Lys
1               5
```

DISPLAY OF RECEPTORS AND ANALYSIS OF BINDING INTERACTIONS AND DRUG LIBRARIES

CROSS-REFERENCE TO RELATED APPLICATIONS

This application is a divisional application of U.S. patent application Ser. No. 09/370,358, entitled Display of Receptors and Analysis of Binding Interactions and Drug Libraries, filed Aug. 9, 1999 now U.S. Pat. No. 7,018,846, which claims the benefit of the filing of U.S. Provisional Patent Application Ser. No. 60/096,010, entitled Solid Phase Display of Combinatorial Libraries and Non-Cellular Display of 7 TMR, filed on Aug. 10, 1998, the entire contents and disclosures of which are hereby incorporated herein by reference.

GOVERNMENT RIGHTS

The U.S. Government has a paid-up license in this invention and the right in limited circumstances to require the patent owner to license others on reasonable terms as provided for by the terms of Contract No. R29Al36357 awarded by U.S. NIH, Contract No. R01Al40115 awarded by U.S. NIH, Contract No. 96009620 awarded by U.S. AHA, and Contract No. RR01315 awarded by U.S. NIH.

BACKGROUND OF THE INVENTION

1. Field of the Invention (Technical Field)

The present invention relates to non-cellular display of 7-transmembrane receptors on beads or in suspension, and their use in flow cytometry or multi-well fluorescence or resonance energy transfer to evaluate ligand discovery, especially within combinatorial libraries. The invention is also a method to use the above constructs and protocols to detect real-time receptor-G-protein interactions or interactions between receptors and other intracellular components.

2. Background Art

Much of modern biomedical research, including drug discovery, involves the analysis of molecular interactions, such as those between receptors and ligands, enzymes and substrates, and drug compounds and their cellular targets. Receptors are of particular interest, as signal transduction via these biological mediators controls such processes as cell growth, movement and function. Development of a system for homogeneous receptor study would allow analysis of stoichiometry, affinity, and kinetics, as well as the elucidation and characterization of signal transduction complexes.

One of the largest families of receptors in the human genome is that of the 7 transmembrane (7 TMR) superfamily, also known as G-protein coupled receptors, numbering approximately 2000. More than 40% of the current drugs on the market target one or more of these receptors. One of the better studied of these receptors is the N-formyl peptide chemoattractant receptor (FRP) and it serves a model system for the entire family. It is largely responsible for numerous immune functions. In addition, 7-TMR have been shown to be docking sites for HIV entry into white blood cells, and are known to be important in asthma as well as the diagnosis and treatment of neuro-endocrine cancer.

7-TMR 10 have seven transmembrane α-helical domains 12, with three connecting loops on each inner and outer face of membrane 14, as shown in FIG. 1. The N-terminal region is extracellular, while the C-terminus is intracellular. The three extracellular loops and transmembrane region participate in ligand binding. Ligands that can stimulate (agonistic) or inhibit (antagonistic) receptor function are primary targets in drug discovery. The intracellular loops, especially the second intracellular loop, and tail, in contrast, participate in interactions with the G-protein. G-proteins are important effectors of cell activation, for example, through the interaction with formyl-peptide receptor-ligand complexes. The pathway of cell activation for monovalent chemoattractant ligands appears to involve the interaction of receptor-ligand complexes with guanine nucleotide-binding proteins (G-proteins). For example, the formyl peptide receptors and other 7TMR in permeabilized cells or cell membranes are sensitive to guanine nucleotides and are able to couple with G-protein. Sklar et al., *Regulation of Ligand-Receptor Dynamics for Guanine Nucleotides*, 262 J. of Biol. Chem. 135–139 (1987).

Traditional methods for examining receptor behavior require a separation step, frequently involving centrifugation or filtration. These steps are not optimal for real-time kinetic analysis of rapidly equilibrating systems.

Earlier assays were developed to study binding interactions. These include U.S. Pat. No. 4,275,149, to Litman et al., entitled Macromolecular Environment Control in Specific Receptor Assays, which discloses the use of beads, and enhancement or diminution of signal (i.e. diffusion or pH change) due to a receptor-ligand interaction, through the use of chromagen and anti-chromagen molecules. The assay does not allow quantitation or elucidation of actual binding events.

U.S. Pat. No. 4,665,020, to Saunders, entitled Flow Cytometer Measurement of Binding Assays, discloses receptors bound to large beads and ligands bound to smaller beads with a label. The two sizes of beads are added together, and analyzed by flow cytometry for largest size of aggregates, representing bound receptor/ligand complexes. This assay eliminates the need for a washing step, but does not have the ability to assess a library of ligands simultaneously bound to beads.

U.S. Pat. No. 5,747,349, to van den Engh et al., entitled Fluorescent Reporter Beads for Fluid Analysis, discloses reporter molecules bound to a fluorescent bead which is sensitive to some aspect of the analyte e.g., pH or oxygen saturation, causing a change in fluorescence. This assay does not detect aggregates.

U.S. Pat. No. 5,405,784, to Van Hoegaerden, entitled Agglutination Method for the Determination of Multiple Ligands, discloses the use of antiligands on latex beads to analyze substances. Different ligands are associated with fluorescence of different colors. This assay does not allow for bound or free receptors to identify ligands on libraries.

U.S. Pat. No. 5,601,992, to Lerner et al., entitled Peptide Library Formats and Methods Relating Thereto, and U.S. Pat. No. 5,698,685, to Summerton et al., entitled Morpholino-Subunit Combinatorial Library and Method, also do not entail a method to quantitate and elucidate specific receptors, and cannot be used with flow analysis for real-time kinetic analysis.

The above inventions lack the ability to detect ligands and drug interactions in real-time kinetic assays, and do not examine the possibilities of such assays with 7-TMR. The present invention successfully addresses these issues by utilizing beads or micelles to display 7-TMR for flow cytometry and resonance energy transfer (RET) assays to determine the effect various drugs (expressed in combinational libraries or individually in solution) have on the binding capacity, and ultimately the enzymatic activities in receptor signal transduction and termination. It also allows for examination of molecular mechanisms with purified proteins under physiologically meaningful conditions and with known stoichiometry. The display and assays provided by the present invention allow an important sequence of signaling events (ligand binding, receptor and G-protein coupling, and receptor desensitization) to be evaluated as drug targets.

SUMMARY OF THE INVENTION
(DISCLOSURE OF THE INVENTION)

The present invention is a method for non-cellular display of 7-transmembrane receptors comprising the steps of incorporating an attachment scheme to a receptor, solubilizing the receptor, and presenting the receptor in conjunction with a support. Preferably, a C-Histidine, N-Histidine, biotin, or GST tag is incorporated, preferably into an oligonucleotide, and preferably into an FPR construct prior to amplification. The receptor is preferably solubilized by lysing cell membranes containing the receptor. Preferably, the receptor is presented by affinity coupling the receptor to a particulate substrate, preferably on a silica bead, or latex, or other bead substrate appropriate for flow cytometry and more preferably on a $Ni^{2+}$ silica bead.

In an alternative embodiment, the method further comprises the step of presenting at least one ligand to bind to the receptor, preferably on a support, and preferably a library of ligands. The method alternatively further comprises the step of combining the receptor and ligand to accomplish binding. Preferably, the ligand is associated with a magnetically labeled support, and alternatively the ligand is fluorescently labeled or alternatively the receptor is fluorescently labeled.

In a preferred embodiment of the present invention, the method further comprises the step of sorting the bound receptor ligand pairs by fluorescence. Preferably, they are sorted by flow cytometry, more preferably by size, and alternatively they are sorted by magnetic field. In an alternative embodiment of the invention, the method further comprises the step of presenting a soluble or bead-bound molecule to block the binding of the receptor with the ligand. Preferably at least one drug is presented. In an alternative embodiment of the present invention, the receptors are presented in conjunction with a micelle.

The present invention is also a method for ligand interaction analysis and drug discovery comprising the steps of presenting a receptor within a micelle, presenting a ligand on a bead to associate with the receptor, presenting a molecule to be studied to displace the receptor from the ligand, and measuring the resonance energy transfer resulting from the displacement. Preferably, a soluble receptor is incorporated into a micelle. Alternatively, the receptor is preferably tethered, preferably to beads via affinity tags or phospholipid bilayer. The receptor is preferably associated in the micelle with a fluorescent acceptor, preferably rhodamine, Texas Red or Fast Di-I. Alternatively, the receptor has fluorescence incorporated, preferably as association with a GFP chimera. In a preferred embodiment of the present invention, a ligand is soluble, and preferably is conjugated to a fluorescent donor, and more preferably fluorescein.

In a preferred embodiment of the present invention, the method further comprises the step of detecting ligand binding to receptor using resonance energy transfer (RET), preferably by flow cytometry, plate reader, or spectrofluorometer, and preferably the binding of ligand to receptor by using resonance energy transfer (RET) between the fluorescent donor ligand and the fluorescent acceptor associated with the receptor or the micelle.

Preferably, a soluble molecule to be studied is presented to displace the receptor from the ligand, and alternatively a library of molecules is presented, preferably a library of drug molecules, more preferably on a support, and most preferably on a bead. Preferably, the step of measuring the resonance energy transfer resulting from the displacement comprises measuring a diminished RET signal, preferably measured using ratiometric detection, and preferably includes measuring using flow cytometry to identify bound molecules. Preferably the method further comprises after presenting a ligand, the step of exposing the receptor to G-protein. The invention also comprises a drug discovered by the process comprising the steps of presenting a receptor within a micelle, presenting a ligand on a bead to associate with the receptor, presenting the drug to be studied to displace the receptor from the ligand, and measuring the resonance energy transfer resulting from the displacement.

A primary object of the present invention is to provide a display of 7-TMR that can be utilized in both flow cytometry and multiwell plate analysis for kinetic studies of binding interactions;

Another object of the present invention is to provide a method for ligand discovery;

A further object of the present invention is to provide a method for discovering receptor G-protein, receptor kinase or receptor arrestin, blocking agents;

Still another object of the present invention is to provide a method of receptor-binding detection that does not utilize a fluorescent ligand.

A primary advantage of the present invention is to elucidate binding interactions in real-time studies without a washing step;

Another advantage of the present invention is the ability to rapidly screen large combinatorial drug libraries;

Yet another advantage of the present invention is the ability to isolate and analyze the receptor in a single step procedure; and A further advantage of the present invention is the ability to quickly screen solubilized drugs for effects on binding and signal transduction actions.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
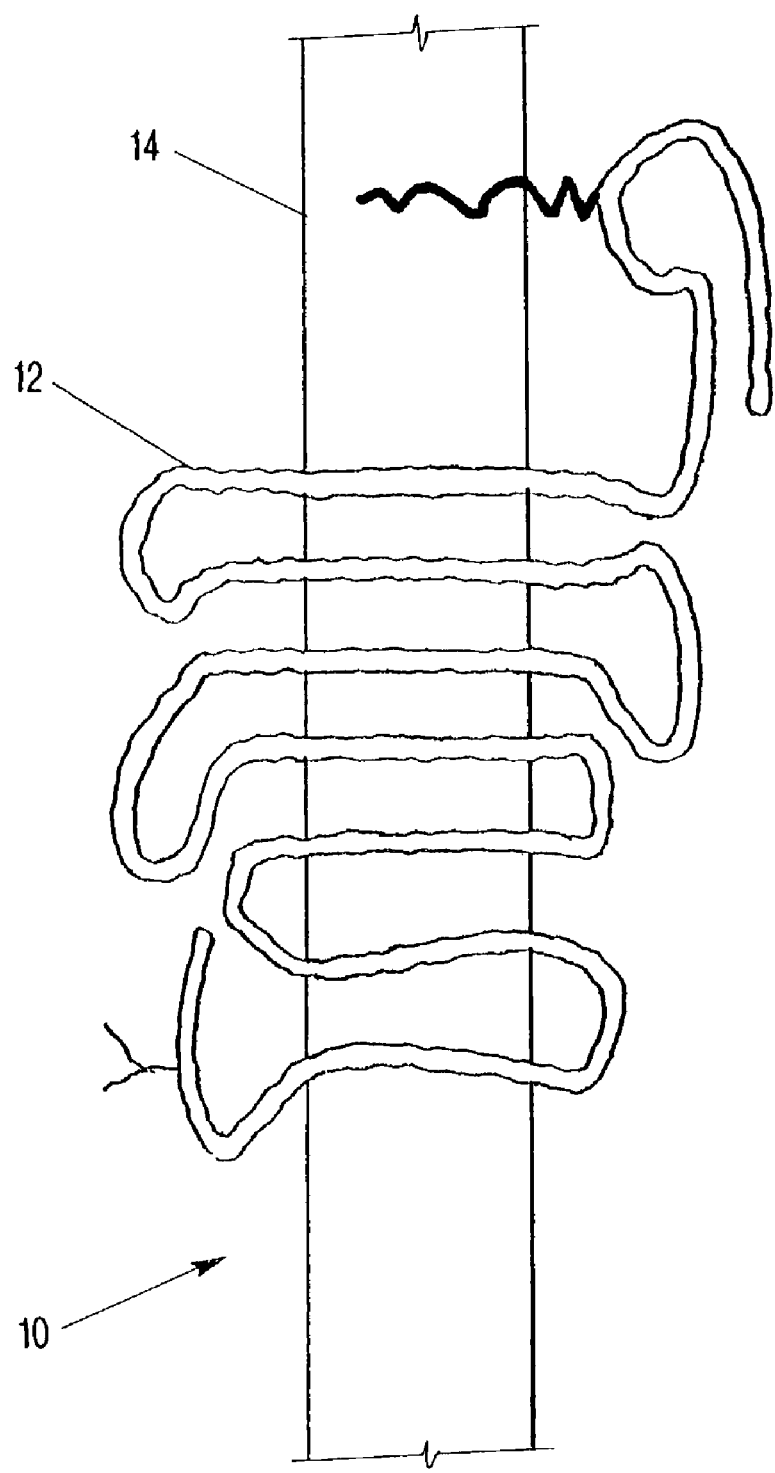
FIG. 1 is a cross-sectional view of a 7 transmembrane receptor spanning a membrane.

DESCRIPTION OF THE PREFERRED EMBODIMENTS BEST MODES FOR CARRYING OUT THE INVENTION

The present invention comprises a novel display of 7-transmembrane receptors (TMR) for use in bead or micelle systems to detect binding and subsequent G-protein interactions in response to various molecules, i.e. drug libraries. They allow for real-time kinetic analysis by eliminating a washing and pelleting step. The receptors (FPR or His$_6$ FPR, e.g.) are generated by PCR amplification of existing or mutant constructs of FPR. The constructs are then transfected into cells, which are tested for expression and function. In order to examine receptor molecular assemblies, broken cell preparations such as membranes and permeabilized cells are used to allow access to both intracellular and extracellular receptor faces. Preferably, membranes are prepared from the cells expressing the wild type or C-terminally His-tagged N-formyl peptide receptors, and the receptors solubilized in dodecyl maltoside. The solubilized receptors are then ready for use in bead assays or micelle assays.

For presentation on beads, the receptors are bound to Ni$^{2+}$ silica beads or other derivatized microspheres of appropriate composition, and then are detected in the flow cytometer. When FPR are bound to beads using either the N-His or C-His tags, they are able to bind fluorescent ligand. (Other attachment schemes, such as biotin or GST tags, are also appropriate.) The N-His receptor can be used where the "extracellular face" of the receptor is in proximity to the bead and the intracellular face is away from the bead and consequently available to the G-protein. The bound bead is then used in ligand discovery.

In one embodiment, fluorescence is used to analyze ligand binding and dissociation with membranes and solubilized receptors. This involves a fluoresceinated ligand and an antibody to the fluorescein which discriminates free and receptor-bound ligand by rapidly quenching the fluorescence of the free ligand and quenching the fluorescence of the receptor-bound ligand only after it dissociates from the receptor. The quantity of receptor-bound peptide can be determined as the observed fluorescence of the sample immediately following addition of the anti-fluorescein antibody.

The receptor binds fluorescent ligand specifically in a concentration range consistent with endogenous receptor expressed on the surface of neutrophils. Site density of the FPR on the beads is controlled by amounts of soluble protein added to the beads. Receptor-coated beads can be kept at 4° C. for extended periods of time, and can then be used in a variety of receptor binding studies. For example, the receptors can be used in ligand binding studies based upon fluorescent or magnetic labeling, and such binding pairs can be detected/selected by resetting and subsequent flow cytometry sorting or magnetic sorting.

Yet another advantageous use of receptors displayed on beads or solubilized including 7-TMR, is ligand discovery by resonance energy transfer (RET). In RET, a signal arising from the association of a ligand-receptor pair (fluorescent donor on the ligand and a fluorescent acceptor associated with the display system, or when the pair is on beads, acceptor associated with the ligand and donor associated with the receptor or micelle) is sensitive to the presence of a soluble or bound ligand in competition with the binding between the tethered components. Ligand binding can be followed as a change in bulk fluorescence signal resulting from energy transfer between the ligand and the micelle. This system allows detection and analysis of molecular assemblies in multi-well plate and flow cytometry based assays.

Figure 6:
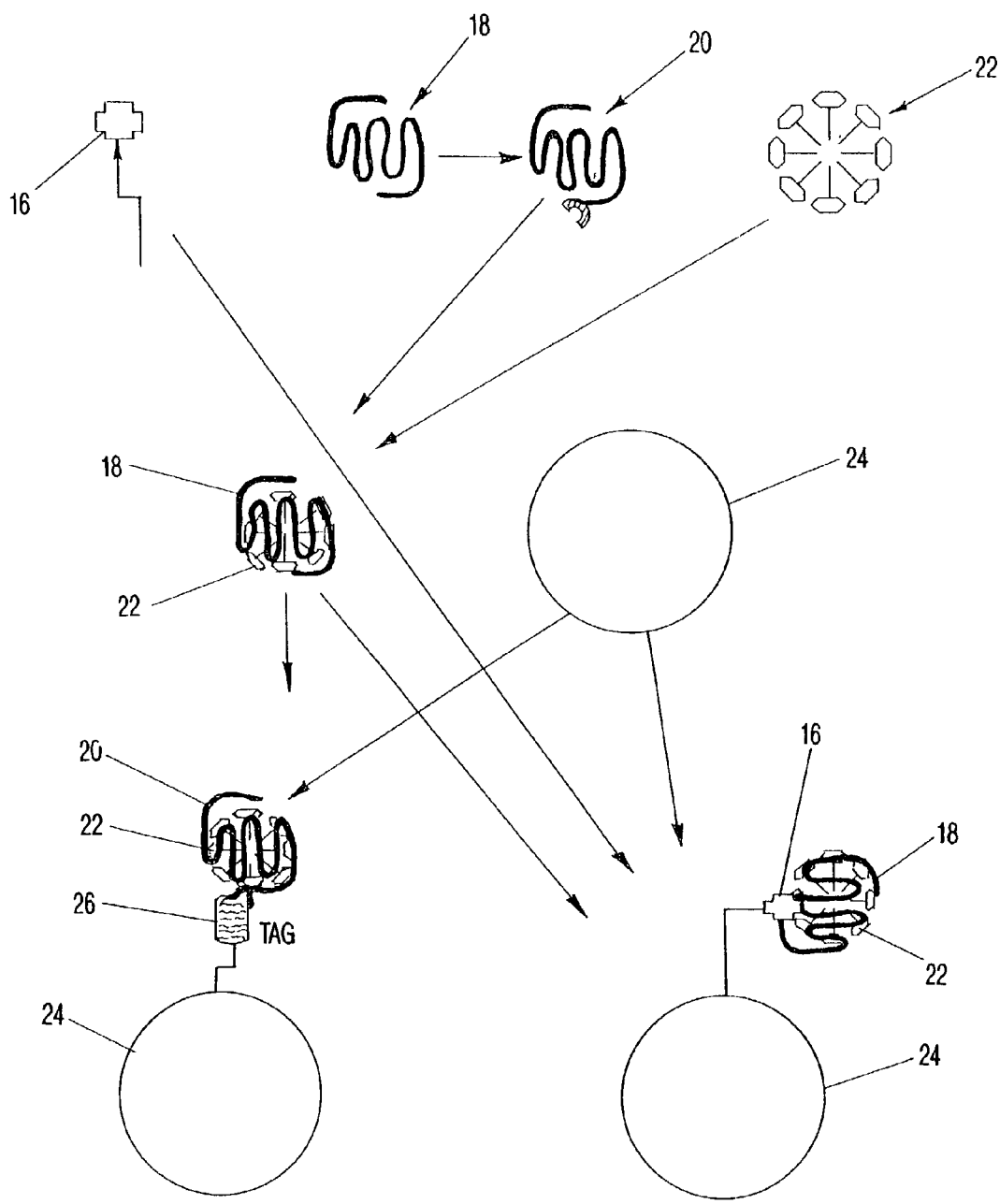
FIG. 6. is a diagrammatic of the detection components with ligand, receptor, micelle, beads and assembled components.

While it is possible to detect the binding of small molecules to beads directly by their fluorescence or indirectly through competition with fluorescent molecules, there are obvious advantages to having detection schemes in which all the fluorescence components are in the receptor display itself. FIG. 6 shows a situation in which if the fluorescence acceptor is in the micelle, the RET signal results from association of donor ligand with the micelle.

The receptors are solubilized into DOM micelles. In this use of RET, the association of the fluorescent probe such as Fast Di-I or rhodamine lipid partitioned into a detergent micelle, would confer the fluorescence to the micelle. Only the micelles having associated receptors are capable of binding beads. The association of the receptor with the ligand on the bead confers the specificity of the capture. The association of the receptor and its corresponding fluorescent micelle generates the fluorescent signal. The selected receptors can then be used to identify libraries on beads. The association of the ligand with the particle surface is detected by RET between the ligand and the fluorophores associated with the bead surface. In the case of bead-bound libraries, only beads that display ligands in the library will bind the receptor micelles and thereby become fluorescent. The receptor-associated fluorescence then moves from the small ligand bead to the large library bead where it can be sorted.

Alternatively, the soluble receptor is either originally in a micelle with an acceptor for ligand fluorescence, or the receptor has fluorescence incorporated or embedded into the receptor (e.g. GFP chimera). If the receptor binds to the drug, the pair fluoresces. In the presence of soluble combinatorial libraries, the specific binding of receptors to ligands in micelles or beads is inhibited. By examining the number of receptors on beads as a function of the input receptor concentration, the binding constant between the receptor in the micelle and the ligand on the bead can be determined. Also, by examining the fluorescence signal in micelles or beads as a function of drug concentration, the binding constant of the drug can be determined. This approach is extended to study drugs that block the increased binding of the receptor and ligand in the presence of G-protein using RET between ligand donor and micelle acceptor.

The presence of G-protein increases the binding of the ligand and the receptor. When G-protein is incubated with the receptor, the ligand dissociation becomes slower. This rate increases again with the addition of guanine nucleotide such as GTPγS. The ligand affinity is also increased with the presence of the nucleotide. To determine if potential drug molecules are capable of disrupting receptor-G-protein complexes, receptors are assembled to G-proteins in the presence of fluorescent ligand. G-protein concentration is in the nM to μM range. Following incubation of minutes to hours, the association of G-protein with receptors is verified either in a direct measurement of G-protein fluorescence on beads or indirectly with ligand dissociation rate. This approach can be used to distinguish ligands which are agonists and promote receptor-G-protein coupling, and antagonists which do not. The approach can also be used to identify drugs which block receptor-G protein interaction and those which do not. In particular, antagonists will interfere with ligand binding but will not be affected by the presence of G protein; agonists will interfere with ligand binding when G protein is present or absent; and drugs which target G protein receptor interaction will block ligand receptor interaction when G protein is present but not when absent.

INDUSTRIAL APPLICABILITY

In the following examples, plasticware was obtained from VWR Scientific Company (West Chester, Pa.). Chemicals and reagents were obtained from Sigma (St. Louis, Mo.) except where otherwise noted. U937 cells (human histiocytic lymphoma) were obtained from American Type Culture Collection (ATCC, Rockville, Md.). Cells were grown in tissue culture treated flasks (Corning, Corning, N.Y.) in RPMI 1640 (Hyclone, Logan, Utah) containing 10% FBS, 2 mM L-glutamine, 10 mM HEPES, with 10 U/ml penicillin and 10 μg/ml streptomycin. Cultures were grown in standard tissue culture incubators at 37° C. with 5% $CO_2$, and passaged from subconfluent cultures every 2–3 days by reseeding at $2 \times 10^5$ cells/ml.

EXAMPLE 1

The hexahistidine tag was incorporated into a C-terminal oligonucleotide. This oligonucleotide was used in conjunction with an N-terminal oligonucleotide and pfu polymerase for PCR amplification of the FPR. Automated dideoxy sequencing was performed to confirm the sequence. The receptor-tagged constructs were transfected into U937 cells by electroporation and selected with G418. The transfected cells were identified by fluorescent peptide binding and sorted by flow cytometry. In typical preparations, the receptor density was determined using fluorescent peptide and flow cytometric analysis to be ~300,000 per cell.

U937 C-His FPR cells were harvested, centrifuged at 200×g for 5 minutes and resuspended in cavitation buffer at a density of $10^7$ cells/ml at 4° C. (10 nM PIPES, 100 mM KCl, 3 mM NaCl, 3.5 mM $MgCl_2$, 600 μg/ml ATP, 50 μM PMSF, 20 μg/ml chymostatin, and 0.05% DFP). The cell suspension was placed in a nitrogen bomb and pressurized to 450 psi using $N_2$ gas for 20 minutes at room temperature. Unlysed material was separated by centrifugation at 1000×g for 5 minutes at 4° C. The supernatant, containing membranes, was washed twice by centrifugation at 135,000×g for 30 minutes at 4° C., then resuspended in HEPES sucrose buffer (200 mM sucrose, 25 mM HEPES, pH 7), aliquoted, and stored at −80° C. until use.

Lysed membranes were thawed and diluted to $1–2 \times 10^8$ membrane cell equivalents/ml (CEQ/ml) in binding buffer (BB, 30 mM HEPES, 100 mM KCl, 20 mM NaCl, 1 mM EGTA, 0.1% w/v BSA, 0.5 mM $MgCl_2$, 1 mM PMSF). Preparations were maintained at 4° C. throughout the extraction process.

EXAMPLE 2

Membranes from transfected cells expressing C-terminal His-tagged N-formyl peptide receptors were prepared as above. Membranes were centrifuged at 135,000×g for 30 minutes and resuspended to $6 \times 10^8$ CEQ/ml in BB containing a broad protease inhibitor cocktail (Calbiochem, La Jolla, Calif.) and 1% n-dodecyl β-D-maltoside (DOM). Preparations were incubated 60 minutes at 4° C. with agitation. The insoluble fraction was separated by centrifugation at 87,750×g for 30 minutes. The supernatant was removed, and this extract was used for experimentation.

To affinity-couple formyl peptide receptors to a particulate substrate, $Ni^{2+}$-nitriloacetate coated silica particles (Ni-NTA, Qiagen, Santa Clarita, Calif.) were added to U937 C-His FPR membrane extracts at 10 mg/ml and incubated at 4° C. for 30 minutes with gentle mixing. This concentration of silica produced $1.15 \times 10^6$ silica particles/ml as measured using a hemocytometer. Silica particles ranged from approximately 2–20 μm in diameter with random non-spherical shapes. Since silica particles settle rapidly from suspension, samples required gentle resuspension by inversion or pipetting at each handling step.

Figure 2A:
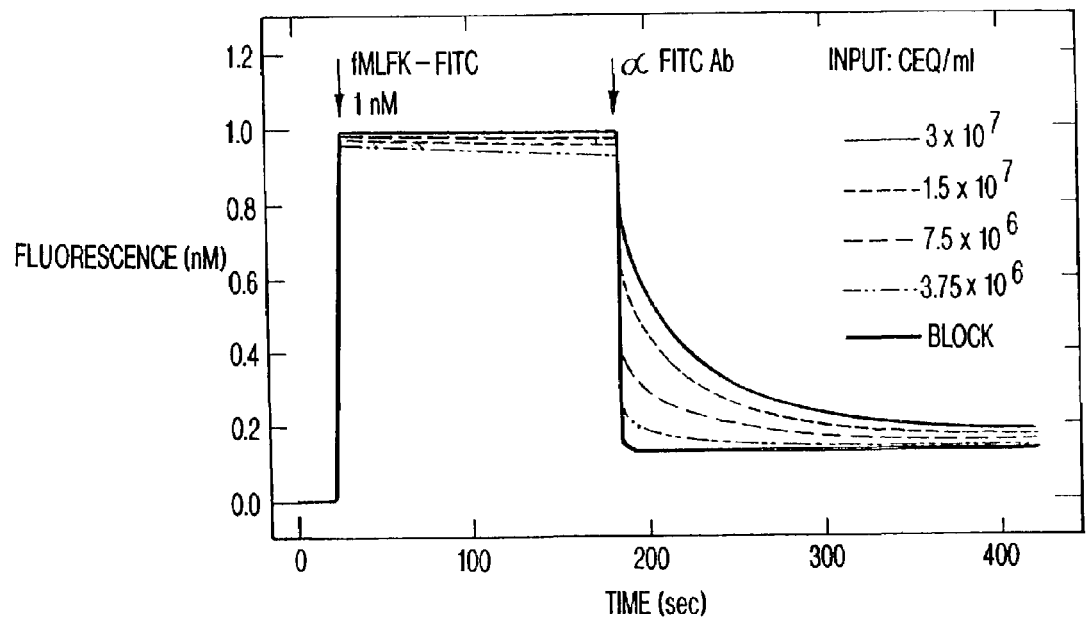
FIG. 2a is a graph showing the ligand fluorescence of membrane preparations as a function of receptor input.
Figure 2B:
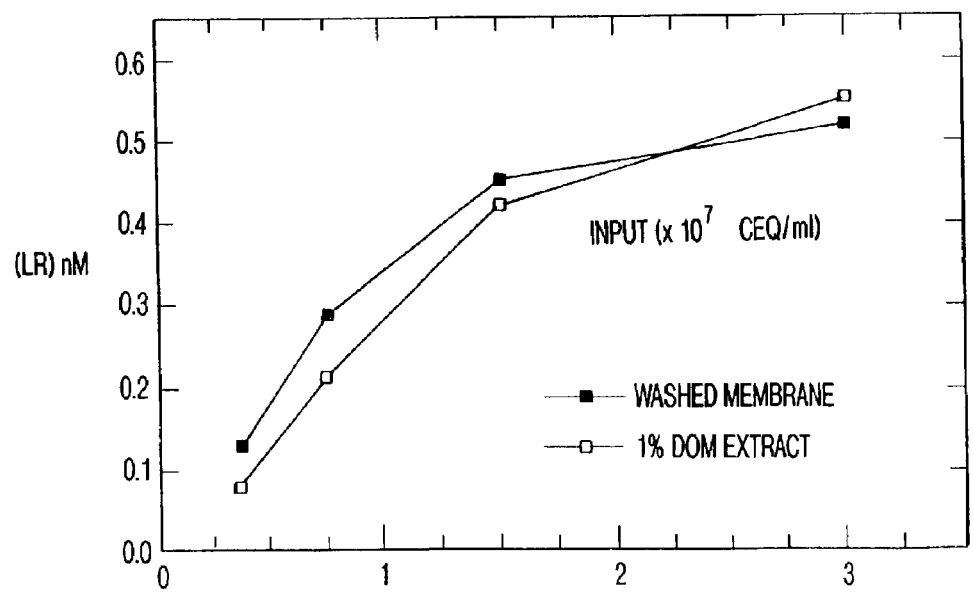
FIG. 2b is a graph showing the amount of ligand bound in membrane versus solubilized extracts.

Following preparation at 4° C., samples were equilibrated to 22° C. and placed into the spectrofluorometer with constant stirring. Fluorescence associated with formyl-met-leu-phe-lys-FITC (fMLFK-FITC, Peninsula Laboratories, Belmont, Calif.) was measured by a SLM 8000 spectrofluorometer (Spectronic Instruments, Rochester, N.Y.) using the photon counting mode in acquisition. Data were acquired for 200–420 seconds in 1-second intervals. Typically, background fluorescence was obtained for the first 20 seconds, fMLKF-FITC was added, and fluorescence was measured to 180 seconds. Then, an antibody recognizing fluorescein was added to the sample. Binding was detected as residual fluorescence following addition of antibody to fluorescein. Data for each separate curve represented a varied 7-TMR receptor input expressed as the quantity of receptors present in a sample of extracted membranes prepared from an equivalent number of cells/ml (CEQ/ml). The antibody bound fMLFK-FITC with high affinity and resulted in essentially complete quenching of fluorescence associated with free ligand. Thus, the remaining fluorescence represented the bound fraction and was used to estimate the concentration of bound ligand. FIG. 2a shows the behavior of the membrane extract in an assay with 1 nM fluorescent formyl peptide as a function of receptor input. FIG. 2b shows comparison of the amount of ligand bound in the assay for membranes and solubilized membrane extracts (determined as in Panel A) as a function of the amount of membrane used. (Note that if 20% of the cellular receptors (~300,000/cell) are recovered in the membrane preparation and solubilization steps, $10^7$ CEQ/ml would provide about 1 nM receptors.)

EXAMPLE 3

Figure 3A:
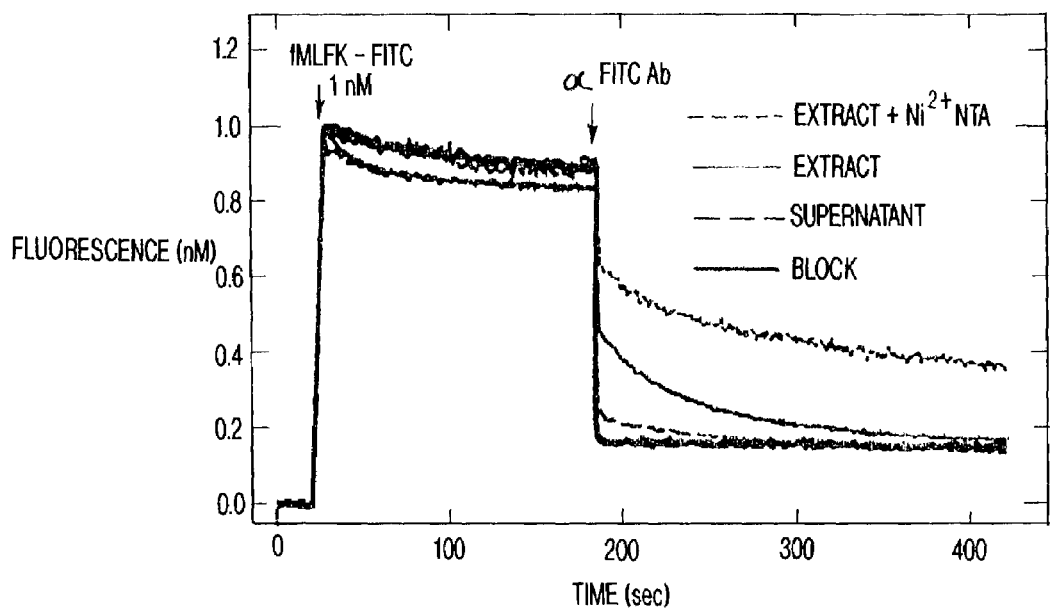
FIG. 3a is a plot showing the fluorescence of Ni$^{2+}$ silica particle incubated with receptors.
Figure 3B:
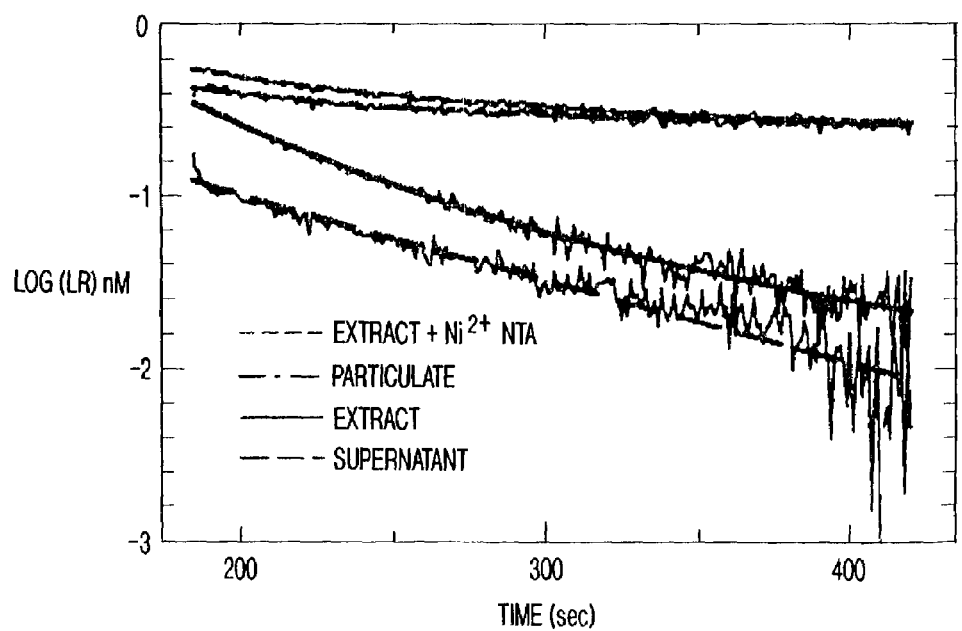
FIG. 3b is a plot comparing ligand-receptor dissociation characteristics for soluble and bead bound receptors.

The solubilized receptors were displayed on silica particles in a format compatible with flow cytometry. FIG. 3a shows the results of a receptor recovery assay in which the particles were incubated with solubilized receptors. The uptake of C-His FPR onto $Ni^{2+}$-NTA silica particles was demonstrated by the depletion of receptor from FPR extracts. The experiments were performed with 1 nM fMLFK-FITC, $1.5 \times 10^7$ cell equivalents/ml of membrane and 20 mg silica particles/ml. The spectroscopic analysis used the antibody to fluorescein to examine ligand binding. The binding curves are depicted from top to bottom: receptors present on silica particles, receptors present in the membrane extract, receptors present in the supernatant after silica particles have been removed from the extract, control sample in which a blocking peptide ($10^{-5}$ M tboc-phe-leu-phe-leu-phe) (SEQ ID NO. 1) inhibits the specific binding. In the presence of the particles, receptors were quantitatively sedimented out of bulk phase. Binding of ligand to the particle-bound receptors resulted in an increased ligand binding signal (due to slower ligand dissociation and a higher binding affinity). FIG. 3b compares the ligand-receptor dissociation characteristics. Dissociation rates are determined from FIG. 3b by subtracting the non-specific binding in the blocked control from the specific binding and replotting the data on a semi-log scale. From top to bottom the curves are: the ligand dissociation from receptors in the membrane extract in the presence of the silica particles; the ligand dissociation in the particulate fraction of the extract after pelleting by centrifugation and resuspension; the ligand dissociation from solubilized receptors; the ligand dissociation from the supernatant of particles and solubilized receptors.

Figure 3C:
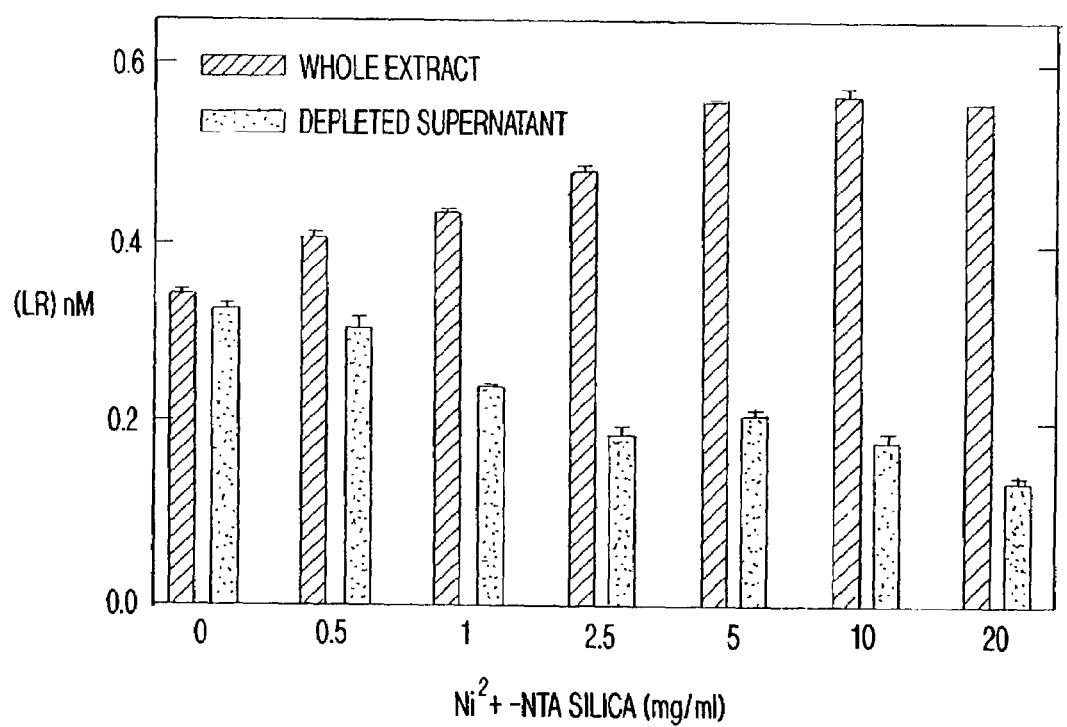
FIG. 3c is a plot showing the uptake of receptor by the Ni$^{2+}$ silica particles.

Based on the nearly linear rate of dissociation, the receptors displayed on the particles were essentially homogeneous. FIG. 3c shows the uptake of receptor by the particles as a function of the particle density. The increase in total ligand binding compared to the membrane extract, as more $Ni^{2+}$-NTA is added, was a consequence of the increase in ligand affinity seen in FIG. 3a. About half of the receptor (~0.2–0.3 nM) was bound by the silica particles at a concentration as low as 1 mg/ml particles. More than 80% of the receptor was bound at 20 mg/ml particles. The reported binding capacity of the particles was approximately 500 pmol/mg, indicating that excess unused binding sites on the particles were present under these conditions. Since the number of receptor binding sites on the particles represent several million per particle, the amount of receptor displayed on the particle depended on the receptor input relative to the particle density. The level of receptor remaining in the supernatant was consistent with a $K_d$ in the nM range between the his-tagged receptor in detergent and the $Ni^{2+}$-NTA binding sites on the particle.

EXAMPLE 4

Figure 4A:
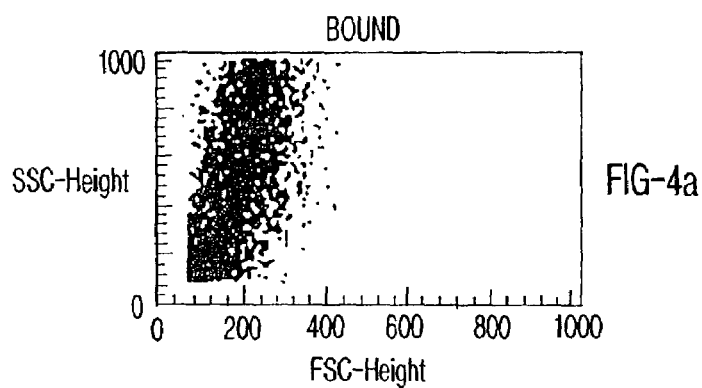
FIG. 4a is a flow cytometric light scatter plot showing characteristics of silica particles in the presence of specific ligand binding, showing that particles are heterogeneous.
Figure 4B:
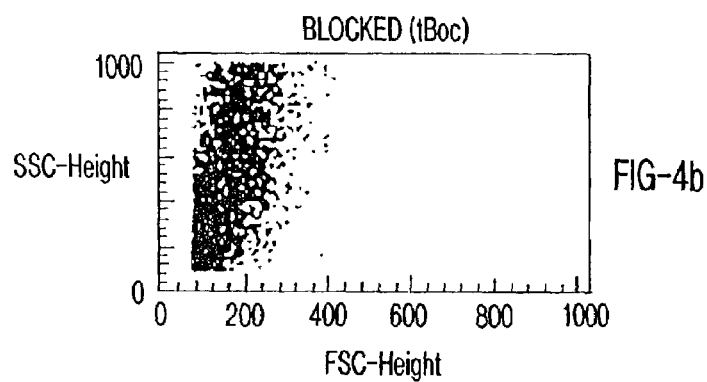
FIG. 4b is a flow cytometric light scatter plot showing characteristics of silica particles in the presence of non-specific ligand binding.
Figure 4C:
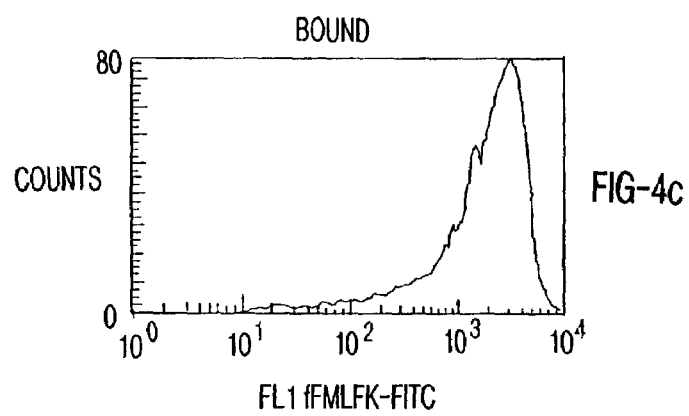
FIG. 4c is a fluorescence histogram of specific ligand binding.
Figure 4D:
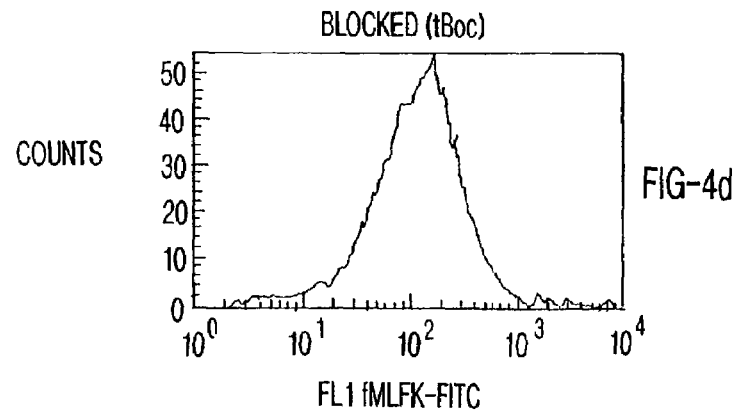
FIG. 4d is a fluorescence histogram of non-specific ligand binding in the presence of antagonist.
Figure 4E:
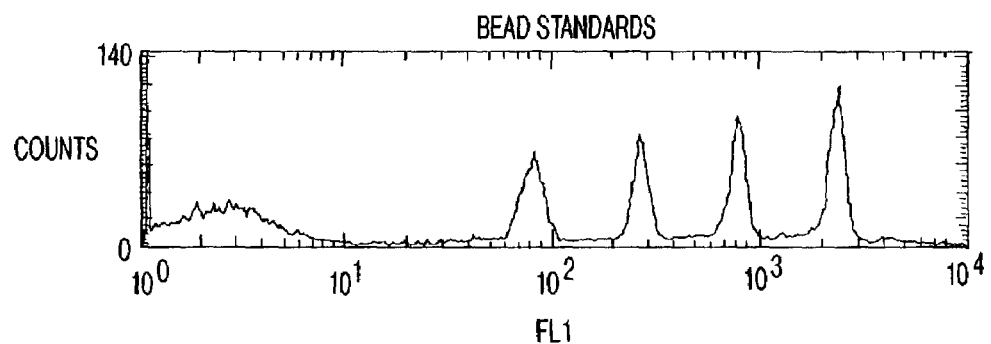
FIG. 4e is a fluorescence histogram of quantitative bead standards.
Figure 4F:
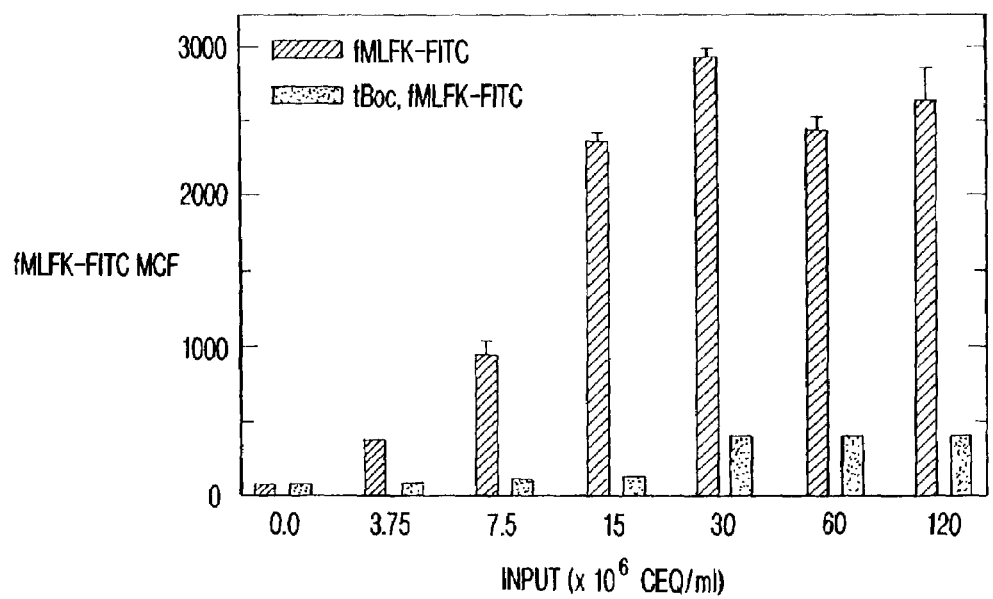
FIG. 4f is a plot showing the various ligand signal to background ratios of different receptor input.

Experiments to assess the quantitative affinity-coupling of soluble C-his FPR to $Ni^{2+}$-NTA silica particles and the relative affinity of the receptor on the substrate for ligand were performed using a FACScan flow cytometer (Becton Dickinson Immunocytometry, San Jose, Calif.). Ten thousand events were analyzed per sample, using a threshold on forward angle light scatter and forward angle versus 90° light scatter dot plot gating to resolve the primary population of silica particles. Data was collected from FL1 (FITC fluorescence) in log mode with no spectral compensation. FIGS. 4a and 4b show light scatter characteristics of silica particles by flow cytometry in the presence of specific (a) and non-specific (b) ligand binding. Fluorescence histograms of specific (FIG. 4c) and non-specific (FIG. 4d) ligand binding were compared to (FIG. 4e) fluorescence histograms of quantitative bead standards. The flow cytometric dot plot of SSC vs FSC shows that the particles are heterogeneous (FIGS. 4a and b). However, the FL1 histogram data shows that there is specific ligand binding (FIG. 4c), compared to the non-specific binding signal obtained when antagonist is present (FIG. 4d). An estimate of the number of receptors displayed per particle was made using calibration standards for fluorescein labeled ligands (FIG. 4e). The average number of fluorescein equivalents per particle was about 1.5 million, similar to the highest standard. In order to convert flow cytometer data to ligand binding measurements, several additional factors must be taken into account: the relative fluorescence of free fluorescein compared to conjugated FITC (85%) and the quenching upon binding to the receptor. The number of receptors occupied at particle saturation is therefore estimated to be ~2 million. Taking into account the $K_d$ and the ligand concentration, as described in FIG. 5 below, the total number of binding sites per article is on the order of 3 million. Under optimal conditions, a fluorescent ligand signal to background ratio of at least 30:1 can be obtained (FIG. 4f). The optimal signal is obtained by varying the input of the receptor at fixed particle density with the signal saturation at an input of receptor above 10–15 million cell equivalent/ml. Samples were prepared and analyzed at 4° C. The five bead populations represented 0, 48,900, 87,400, 552,000, and 1,510,000 fluorescein equivalents. Experiments were performed with 10 nM fMLFK-FITC, 10 mg/ml silica particles, and $1.5 \times 10^7$ CEQ/ml. The blocking peptide t-boc-phe-leu-phe-leu-phe (SEQ ID NO. 1) was used at $10^{-5}$ M. Controls included silica particles with no receptor in the presence or absence of fMLFKF-FITC and samples in which the binding of fMLFK-FITC was inhibited by preblocking with t-boc-phe-leu-phe-leu-phe (SEQ ID NO. 1) or F-met-leu-phe-phe-gly-gly-lys (SEQ ID NO. 2).

Figure 5A:
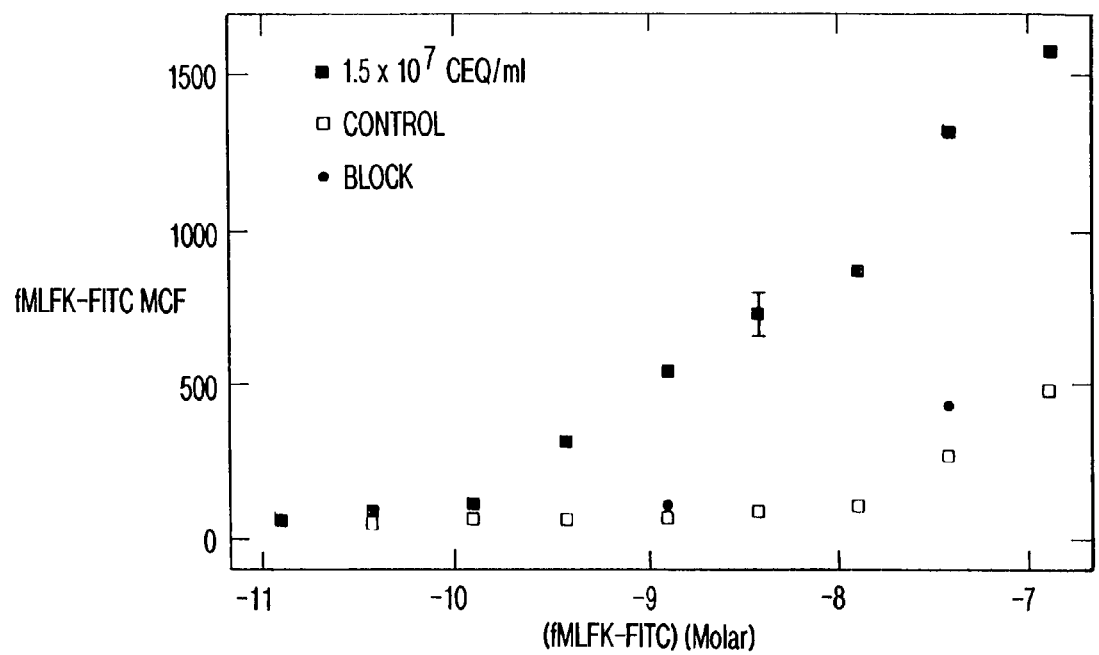
FIG. 5a is a plot showing the function of ligand binding relative to fMLFK-FITC concentration.
Figure 5B:
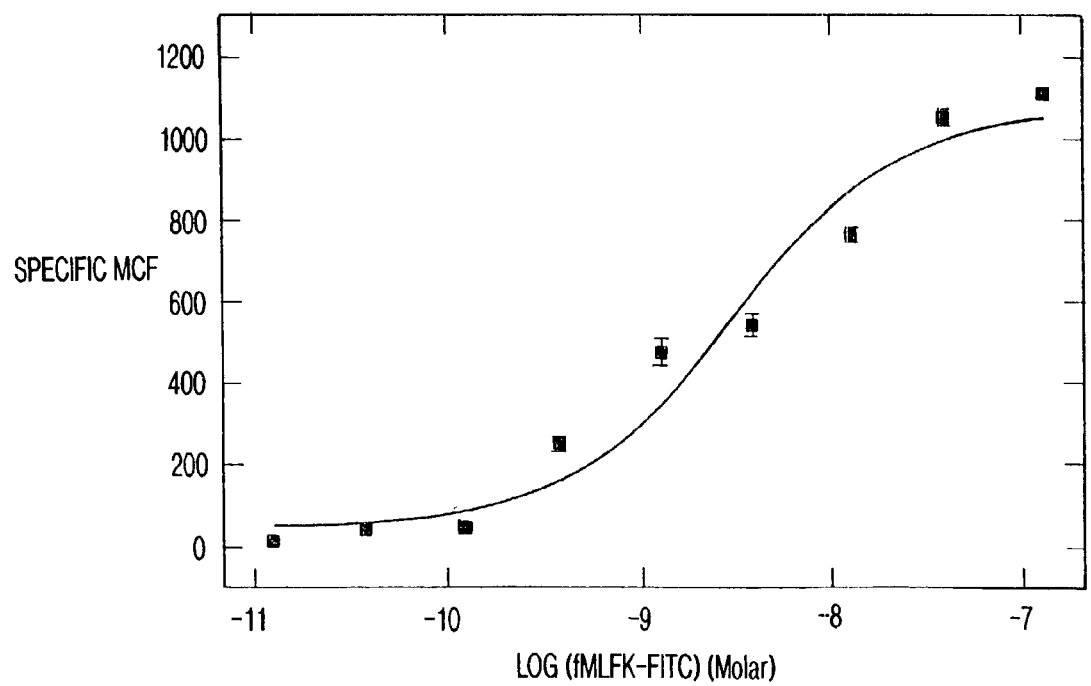
FIG. 5b is a plot showing the estimated $K_d$ of specificity from the sigmoidal dose response curve.

The specificity of ligand binding by FPR was demonstrated by evaluating ligand binding as a function of increasing fMLFK-FITC concentration in flow cytometry experiments, as shown in FIG. 5a. Control experiments examined the signal in the absence of receptor on beads. Blocking experiments were performed in the presence of receptor and 10 μM blocking peptide. As shown in FIG. 5b, the $K_d$ was estimated from the specific fluorescence by fitting the data to a sigmoidal dose response curve. Experiments were performed at $1.5 \times 10^7$ cell equivalents/ml and 10 mg/ml silica particles. (See FIG. 5)

EXAMPLE 5

FIG. 6 shows components of the detection system. These include ligand 16, receptor 18, epitope tagged receptor 20, micelle 22, receptor 18 in micelle 22, bead 24, receptor 18 in micelle 22 on bead 24 with tag 26 or ligand. These can be used with direct or RET fluorescence detection in bulk or flow cytometry. In RET detection, donor and/or receptor and/or micelle and/or bead can be fluorescent. RET can occur between any combination of components. In bulk phase, preferably the donor is on the ligand. In cytometric detection, preferably the acceptor is on the ligand. If additional components bind to the receptors (i.e., G proteins or other intracellular components) they can also be fluorescent.

EXAMPLE 6

Figure 7:
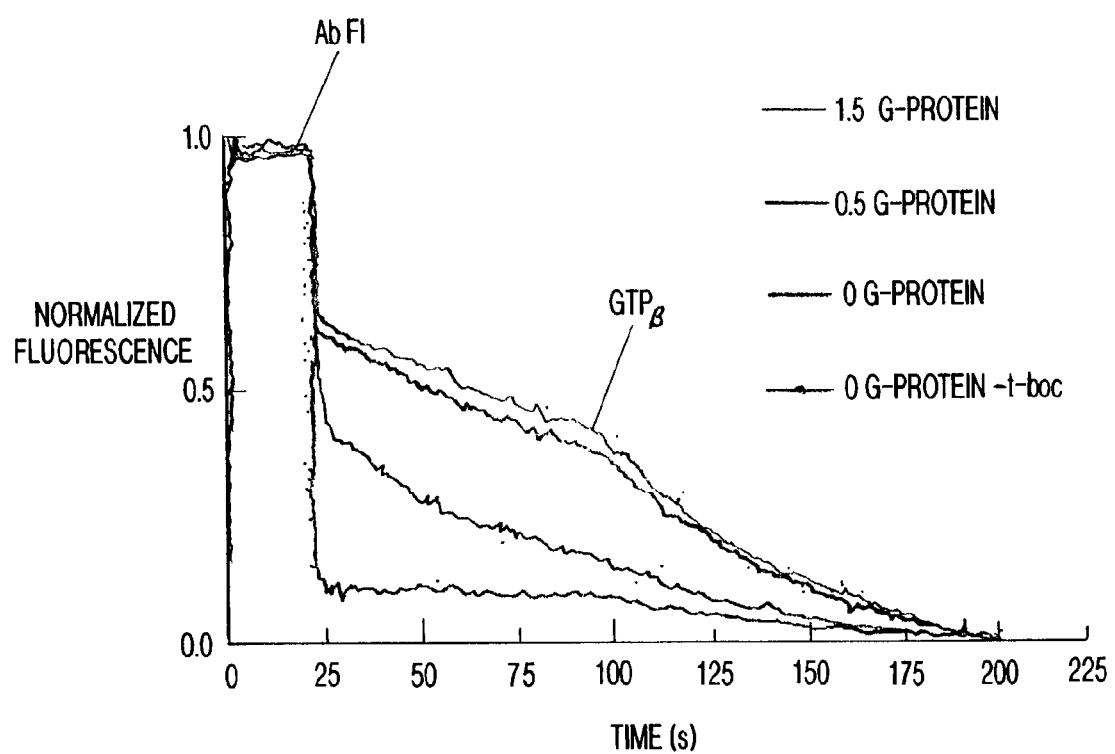
FIG. 7 is a diagrammatic side view of an alternative embodiment of receptor and ligands tethered to a bead, after exposure to a soluble molecule, showing dissociation of peptide and antibody resulting in diminished RET.

Shown in FIG. 7, G-protein was incubated with receptors and 10 nM fluorescent peptide at 37° C. for two hours. The analysis was based upon an antibody to fluorescein which quenches the fluorescence of the free peptide but not the peptide bound to the receptor. In FIG. 7, the lower curve represents a control for non-specific interaction in the presence of a non-fluorescent blocking peptide. This illustrates that when G-protein is incubated with the receptor, the ligand dissociation becomes slower.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

---

---

What is claimed is:

1. A method for non-cellular display of 7-transmembrane receptors comprising the following steps:
   a) incorporating an attachment tether to a receptor;
   b) solubilizing the receptor;
   c) presenting the receptor in conjunction with a support; and
   d) presenting at least one ligand to bind to the receptor, wherein said ligand is known to bind to the receptor and wherein the step of presenting said at least one ligand to bind to the receptor comprises presenting said at least one ligand associated with a magnetically labeled support and said presenting step d) is analyzed with a flow cytometer in real-time.

2. A method for non-cellular display of 7-transmembrane receptors comprising the following steps:
   a) incorporating an attachment tether to a receptor;
   b) solubilizing the receptor;
   c) presenting the receptor in conjunction with a support;
   d) presenting at least one ligand to bind to the receptor, wherein said ligand is known to bind to the receptor;

e) combining the receptor and ligand to accomplish binding; and f) sorting the bound receptor ligand pairs by fluorescence, wherein the steps of presenting said at least one ligand to bind to the receptor, combining the receptor and ligand to accomplish binding and sorting the bound receptor ligand pairs by fluorescence are performed by flow cytometry in real-time.

3. The method of claim 2, wherein the step of sorting the bound receptor ligand pairs by flow cytometry comprises sorting the bound receptor ligand pairs by size.

4. A method for non-cellular display of 7-transmembrane receptors comprising the following steps:

a) incorporating an attachment tether to a receptor;

b) solubilizing the receptor;

c) presenting the receptor in conjunction with a support;

d) presenting at least one ligand to bind to the receptor, wherein said ligand is known to bind to the receptor;

e) combining the receptor and ligand to accomplish binding;

f) sorting the bound receptor ligand pairs by fluorescence; and g) sorting the bound receptor ligand pairs by magnetic field, wherein steps d, e, f and g are performed by flow cytometry in real-time.

5. A method for non-cellular display of 7-transmembrane receptors comprising the following steps:

a) incorporating an attachment tether to a receptor;

b) solubilizing the receptor;

c) presenting the receptor in conjunction with a support;

d) presenting at least one ligand to bind to the receptor, wherein said ligand is known to bind to the receptor; and e) presenting a molecule to block the binding of the receptor with the ligand, wherein said steps d and e aer performed by flow cytometry in real-time.

6. The method of claim 5, wherein the step of presenting a molecule to block the binding of the receptor with the ligand comprises presenting at least one soluble molecule to block the binding of the receptor with the ligand.

7. The method of claim 5, wherein the step of presenting a molecule to block the binding of the receptor with the ligand comprises presenting at least one bead-bound molecule to block the binding of the receptor with the ligand.

8. The method of claim 5, wherein the step of presenting a molecule to block the binding of the receptor with the ligand comprises presenting at least one drug to block the binding of the receptor with the ligand.

* * * * *